United States Patent [19]

Lafon

[11] Patent Number: 4,690,950
[45] Date of Patent: Sep. 1, 1987

[54] 1-[N-(α-AMINO-α-METHYLACETYL-)AMINOPHENYL]-2-AMINOPROPANONE DERIVATIVES

[75] Inventor: Louis Lafon, Paris, France

[73] Assignee: Laboratoire L. Lafon, Maisons Alford, France

[21] Appl. No.: 766,636

[22] Filed: Aug. 16, 1985

[30] Foreign Application Priority Data

Aug. 20, 1984 [FR] France .................. 84 12964

[51] Int. Cl.⁴ .................. C07C 103/50; A61K 31/165
[52] U.S. Cl. ...................... 514/626; 564/196
[58] Field of Search ............... 564/196, 194; 514/626, 514/817, 818

[56] References Cited

U.S. PATENT DOCUMENTS

| | | | |
|---|---|---|---|
| 2,128,255 | 2/1938 | Krizikalla et al. | 564/196 X |
| 4,024,282 | 5/1977 | Kikumoto et al. | 514/651 |
| 4,066,686 | 1/1978 | Lafon | 260/500.5 H |
| 4,128,656 | 12/1978 | Lafon | 514/466 |
| 4,562,211 | 12/1985 | Kikumoto et al. | 514/648 |

FOREIGN PATENT DOCUMENTS 1392584 4/1975 United Kingdom .................. 564/194

OTHER PUBLICATIONS

Lambrou, *Praktika tes Akademias Athenon*, vol. 57, pp. 56–81 (1982).
C. Lambrou, CA 103: 71005m, 9/2/85.

*Primary Examiner*—Charles F. Warren
*Assistant Examiner*—Carolyn S. Greason
*Attorney, Agent, or Firm*—Burgess, Ryan and Wayne

[57] ABSTRACT

The present invention relates to new derivatives selected from the group consisting of:
(i) 1-[N-(α-alkylamino-α-methylacetyl)aminophenyl]-2-alkylaminopropanones of the general formula:

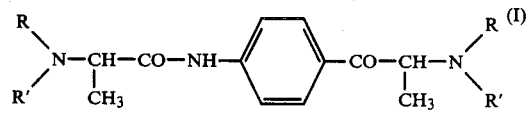

in which R represents a $C_1$–$C_4$ alkyl group and R' represents H or a $C_1$–$C_4$ alkyl group; and
(ii) addition salts thereof.

These new derivatives are useful as CNS-active substances, in particular as stimulants and antidepressants.

The invention also relates to the method for their preparation.

4 Claims, No Drawings

1-[N-(α-AMINO-α-METHYLACETYL)AMINO-PHENYL]-2-AMINOPROPANONE DERIVATIVES

The present invention relates to new 1-[N-(α-amino-α-methylacetyl)aminophenyl]-2-aminopropanone derivatives as industrial products. It also relates to the method for the preparation of these new derivatives and their use in therapy.

It has just been found, surprisingly, that the new derivatives of the formula I below, and addition salts thereof, are useful in therapy as active principles acting on the central nervous system, especially with regard to their antidepressant effects.

The new derivatives according to the invention are selected from the group consisting of:

(i) the 1-[N-(α-alkylamino-α-methylacetyl)aminophenyl]-2-alkylaminopropanones of the general formula:

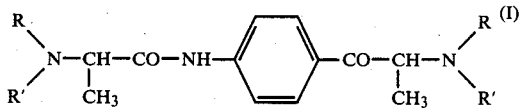

in which R represents a $C_1$–$C_4$ alkyl group and R' represents the hydrogen atom or a $C_1$–$C_4$ alkyl group; and (ii) addition salts thereof.

Among the $C_1$–$C_4$ alkyl groups covered by the definitions of the groups R and R', $CH_2$, $CH_2CH_3$, $CH_2CH_2CH_3$, $CH(CH_3)_2$, $CH_2CH_2CH_2CH_3$, $CH_2CH(CH_3)_2$ and $C(CH_3)_3$ may be mentioned in particular. According to the invention, R will preferably represents $CH(CH_3)_2$, and even more preferably $C(CH_3)_3$, and R' will preferably represents H. The most valuable products from the therapeutic point of view consist of 1-[4-N-(α-tert.-butylamino-α-methylacetyl)aminophenyl]-2-tert.-butylaminopropanone and addition salts thereof.

Addition salts are understood here as meaning, the acid addition salts obtained by reacting a free base of the formula I with a mineral or organic acid, and the ammonium salts. Among the acids which can be used to form salts with the free bases of the formula I, hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular. Among the compounds making it possible to obtain ammonium salts, $CH_3I$ and $CH_3Cl$ may be mentioned in particular. In general, the acid addition salts are preferred to the ammonium salts.

A number of compounds according to the invention are collated in Table I below without in any way implying a limitation.

TABLE I

| Product | Code no. | R | R' |
|---|---|---|---|
| Ex. 1(a) | CRL 41 275 | $C(CH_3)_3$ | H |
| Ex. 2(a) | — | $CH(CH_3)_2$ | H |
| Ex. 3(a) | — | $CH_3$ | $CH_3$ |
| Ex. 4(b) | — | $CH_2CH_3$ | H |

TABLE I-continued

| Product | Code no. | R | R' |
|---|---|---|---|
| Ex. 5(b) | — | $C(CH_3)_3$ | H |

Notes
(a): dihydrochloride
(b): dimethanesulfonate

The compounds of the formula I can be prepared according to a method known per se by the application of conventional reaction mechanisms. The method recommended according to the invention for the synthesis of a compound of the formula I consists in reacting a dihalogen derivative of the formula:

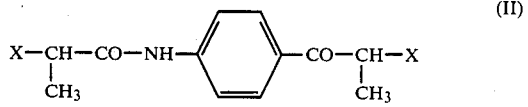

in which X represents a halogen atom selected from the group consisting of F, Cl and Br, the preferred halogen atom being the chlorine atom, with an amine of the formula:

$$HNRR' \qquad (III)$$

in which R and R' are defined as above.

Preferably, more than 2 mol of III will be used per mol of II, the amine III being used simultaneously as reactant and solvent (or co-solvent). The condensation reaction of II with III is carried out for at least one hour at a temperature of between 15° C. and the reflux temperature of the reaction medium. For practical reasons, a mixture of a $C_1$–$C_3$ lower alcohol and the amine III will be used as the solvent.

The compounds of the formula I according to the invention, and salts thereof, are useful in therapy, especially in the treatment of depressive states, on account of their stimulant and antidepressant properties. According to the invention, a therapeutic composition is recommended which contains, in association with a physiologically acceptable excipient, at least one compound of the formula I, or one of its non-toxic addition salts, as the active principle.

Of course, in a composition of this type, the active principle is present in a pharmaceutically effective quantity.

Further advantages and characteristics of the invention will be understood more clearly on reading the following description of a preparative example, which in no way implies a limitation but is given by way of illustration.

PREPARATION

Preparation of 1-[4-N-(α-tert.-butylamino-α-methylacetyl)aminophenyl]-2-tert.-butylaminopropanone dihydrochloride (Example 1; code no.: CRL 41 275)

(a) α-Chloro-α-methylacetanilide 18 g of aniline are introduced dropwise into 22.6 g of 2-chloropropionyl chloride at a temperature of about 10° C., with stirring until the evolution of HCl has ended. After filtration, 31 g (yield: 84.5%) of α-chloro-α-methylacetanilide are obtained in the form of a pink powder. M.p. (inst.)=80° C.

(b) 1-[4-N-(α-Chloro-α-methylacetyl)aminophenyl]-2-chloropropanone

The 31 g of α-chloro-α-methylacetanilide obtained in step (a) above are introduced, at a temperature of between 35° and 45° C., into a mixture consisting of 67 g of $AlCl_3$ and 76.8 g of 2-chloropropionyl chloride. After a contact time of 2 hours followed by precipitation in a water/ice mixture, 40 g (yield: 74%) of 1-[4-N-(α-chloro-α-methylacetyl)aminophenyl]-2-chloropropanone are obtained. M.p. (inst.)=60° C.

(c) CRL 41 275

The 40 g of 1-[4-N-(α-chloro-α-methylacetyl)aminophenyl]-2-chloropropanone obtained in step (b) above are dissolved in 200 ml of ethanol. 200 ml of tert.-butylamine are added to the resulting solution. The mixture is heated under reflux for 8 hours and evaporated in vacuo and the oily evaporation residue is taken up with 200 ml of water. After extraction with $CH_2Cl_2$ and evaporation, the pasty residue is dissolved in ethanol. The expected dihydrochloride is then precipitated with HCl gas. This gives 8.5 g (yield: 10%) of CRL 41 275 in the form of a creamy-white powder. M.p. (inst.) >260° C.

Some of the results of the tests which were undertaken with CRL 41 275 according to the invention have been summarized below.

TESTS RELATING TO CRL 41 275 (PRODUCT OF EXAMPLE 1)

In the neuropsychopharmacological study which follows, a solution of CRL 41 275 in distilled water (pH 5.5) was administered intraperitoneally in a volume of 20 ml/kg to male mice and 5 ml/kg to male rats.

I. TOXICITY

In male mice, the $LD_0$ (maximum non-lethal dose) by intraperitoneal administration is greater than 128 mg/kg and the $LD_{30}$ is of the order of about 250 mg/kg.

II. OVERALL BEHAVIOR AND REACTIVITIES

Groups of three animals are observed before and then 0.25 hour, 0.50 hour, 1 hour, 2 hours, 3 hours and 24 hours after the administration of CRL 41 275. The observations are as follows:

(1°) in mice at doses of 1 to 16 mg/kg:
no distinct modification of the behavior and the reactivities; and at a dose of 64 mg/kg:
sedation (for 2 out of 3 animals) after administration, between T+1 h and T+2 h, with a decrease in the reactivity to touch, and
moderate hypothermia (maximum value: −1.2° C.) between T+2 h and T+3 h;

(2°) in rats at doses of 0.5 mg/kg to 32 mg/kg:
moderate mydriasis for 1 to 2 hours.

III. INTERACTION WITH APOMORPHINE (1°) In mice

Groups of 6 mice receive CRL 41 275 30 minutes before the subcutaneous injection of 1 or 16 mg/kg of apomorphine. It is observed that CRL 41 275 does not modify the hypothermia induced by apomorphine and produces no change in the righting behavior and the stereotypies.

(2°) In rats

CRL 41 275 is administered to groups of 6 rats 0.5 hour before the subcutaneous injection of 0.5 mg/kg of apomorphine. It is observed that CRL 41 275 slightly increases the intensity and duration of the stereotypies induced by apomorphine.

IV. INTERACTION WITH AMPHETAMINE

Amphetamine (2 mg/kg) is injected intraperitoneally into groups of 6 rats 30 minutes after the administration of CRL 41 275. It is found that, at a dose of 32 mg/kg, CRL 41 275 greatly increases the intensity and duration of the stereotypies induced by amphetamine.

V. INTERACTION WITH RESERPINE

Four hours after the intraperitoneal injection of 2.5 mg/kg of reserpine, groups of 6 mice receive CRL 41 275. It is found that CRL 41 275 does not modify the hypothermia and ptosis induced by reserpine.

VI. INTERACTION WITH OXOTREMORINE

CRL 41 275 is administered to groups of 6 mice 0.5 hour before the intraperitoneal injection of 0.5 mg/kg of oxotremorine.

(1°) Action on the temperature

It is found that, at both the strong doses used (16 mg/kg and 64 mg/kg), CRL 41 275 weakly opposes the hypothermic action of oxotremorine.

(2°) Action on the trembling

It is found that CRL 41 275 does not modify the intensity of the trembling induced by oxotremorine.

(3°) Action on the peripheral cholinergic symptoms

It is observed that CRL 41 275 does not modify the signs of peripheral cholinergic stimulation induced by oxotremorine.

VII. ACTION ON THE FOUR PLATE TEST, TRACTION AND ELECTRIC SHOCK

The test is performed on groups of 10 mice 30 minutes after the administration of CRL 41 275. It is found that CRL 41 275 does not modify the number of punished passes, does not cause major motor incapacity and does not modify the convulsant effects, but does seem to aggravate the lethal effects of electric shock at a dose of 64 mg/kg.

VIII. ACTION ON THE SPONTANEOUS MOTILITY 0.5 hour after they have received CRL 41 275, the mice (6 per dose, 12 control animals) are placed in an actimeter, where their motility is recorded for 30 minutes.

It is observed that, at the strongest dose used (64 mg/kg), CRL 41 275 moderately increases the spontaneous motor activity of the mice.

IX. ACTION ON THE INTERGROUP AGGRESSIVENESS

After they have stayed for 3 weeks in the two halves of a cage divided by an opaque partition, groups of 3 mice receive CRL 41 275. Half an hour later, the two groups from the same cage are brought together by removal of the partition, and the number of fights which occur in 10 minutes is noted. Half the test is performed on ordinary mice (NMRI, C.E.R. Janvier) and half on NMRI (Iffa Credo) mice.

It is found that, at a dose of 16 mg/kg, CRL 41 275 reduces the number of fights.

X. ACTION TOWARDS SOME FORMS OF BEHAVIOR PERTURBED BY VARIOUS AGENTS (1°) Motility reduced by habituation to the enclosure After they have stayed in the actimeters for 18 hours, the mice (6 per dose, 12 control animals) receive CRL 41 275. They are immediately returned to their respective enclosures and, half an hour later, their motility is recorded for 30 minutes.

It is observed that, at doses of 4 and 16 mg/kg and especially 64 mg/kg, CRL 41 275 causes a distinct resumption in the motor activity of mice accustomed to their enclosure.

(2°) Motility reduced by hypoxic aggression

Half an hour after they have received CRL 41 275, the mice (10 per dose, 20 control animals) are subjected to acute hypobaric anoxia [pressure reduction of 600 mm Hg (i.e. about $8 \times 10^4$ Pa) in 90 seconds; release of vacuum in 45 seconds] and are then placed in an actimeter, where their motility is recorded for 10 minutes.

It is observed that, at doses of 4 mg/kg, 16 mg/kg and especially 64 mg/kg, CRL 41 275 causes an improvement in the motor recovery of mice whose motility has been depressed following a brief period in a reduced-pressure enclosure. This improvement is more distinct at 4 mg/kg than at 16 mg/kg, but is particularly pronounced at 64 mg/kg.

(3°) Asphyxiant anoxia

Groups of 10 mice receive CRL 41 275 half an hour before the intraperitoneal administration of 32 mg/kg of gallamine triiodoethylate (reference curarizing agent).

It is observed that CRL 41 275 does not modify the time taken for convulsions and death to occur following asphyxiant anoxia caused by a curarizing agent.

XI. INTERACTION WITH BARBITAL

Half an hour after the administration of CRL 41 275, groups of 10 mice receive an intraperitoneal injection of barbital (220 mg/kg).

It is found that (i) at a dose of 64 mg/kg, CRL 41 275 moderately increases the time taken to fall asleep and reduces the duration of the sleep induced by barbital, and (ii) at a weaker dose (16 mg/kg), it slightly reduces the duration of the sleep induced by barbital.

XII. ACTION ON THE "BEHAVIORAL DESPAIR"

Half an hour after they have received CRL 41 275, groups of 6 mice are placed in a beaker filled with water to a height of 6 cm. The total period of immobility between the 2nd and 6th minutes following immersion is noted.

It is observed that, as from a dose of 4 mg/kg, CRL 41 275 causes a statistically significant reduction in the period of immobility of mice which have been forcibly immersed. The reduction in the period of immobility due to despair is very substantial at a dose of 16 mg/kg.

XIII. CONCLUSIONS

The above neuropsychopharmacological tests as a whole show that CRL 41 275 is active in the organism as a stimulant. It has stimulant effects which, although moderate, are of therapeutic value, and antidepressant effects.

In human clinical trials, good results have been obtained in the treatment of endogenous depressions at a daily dose of between 20 and 50 mg, administered orally. The recommended daily dosage for adults consists in administering 3 tablets or gelatine capsules each containing 12 mg of CRL 41 275.

What is claimed is:

1. A 1-[N-(α-amino-α-methylacetyl)aminophenyl]-2-aminopropanone derivative selected from the group consisting of:

(i) 1-[N-(α-alkylamino-α-methylacetyl)aminophenyl]-2-alkylaminopropanones of the general formula:

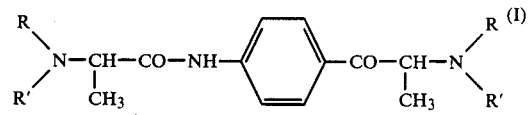

in which R represents $CH(CH_3)_2$ or $C(CH_3)_3$ and R' represents hydrogen; and (ii) addition salts thereof.

2. 1-[4-N-(α-Tert.-butylamino-α-methylacetyl)aminophenyl]-2-tert.-butylaminopropanone and its non-toxic addition salts.

3. A therapeutic composition comprising, in association with a physiologically acceptable excipient, a pharmaceutically effective quantity of a derivative of the formula I according to claim 1, or a non-toxic addition salt thereof.

4. A therapeutic composition according to claim 3, comprising a pharmaceutically effective quantity of 1-[4-N-(α-tert.-butylamino-α-methylacetyl)aminophenyl]-2-tert.-butylaminopropanone or one of its non-toxic addition salts.

* * * * *